(12) United States Patent
Kang et al.

(10) Patent No.: US 11,134,897 B2
(45) Date of Patent: Oct. 5, 2021

(54) APPARATUS AND METHOD FOR MEASURING BIO-INFORMATION

(71) Applicant: SAMSUNG ELECTRONICS CO., LTD., Suwon-si (KR)

(72) Inventors: Jae Min Kang, Seoul (KR); Yong Joo Kwon, Yongin-si (KR); Sang Yun Park, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 628 days.

(21) Appl. No.: 16/004,624

(22) Filed: Jun. 11, 2018

(65) Prior Publication Data

US 2019/0104997 A1  Apr. 11, 2019

(30) Foreign Application Priority Data

Oct. 11, 2017 (KR) .................. 10-2017-0129256

(51) Int. Cl.
*A61B 5/022* (2006.01)
*A61B 5/024* (2006.01)
(Continued)

(52) U.S. Cl.
CPC ............ *A61B 5/6898* (2013.01); *A61B 5/022* (2013.01); *A61B 5/02007* (2013.01);
(Continued)

(58) Field of Classification Search
CPC .. A61B 5/00; A61B 5/02; A61B 5/022; A61B 5/024; A61B 5/6826; A61B 5/746;
(Continued)

(56) References Cited

U.S. PATENT DOCUMENTS 8,761,853 B2 6/2014 Thaveeprungsriporn et al.
2015/0062078 A1* 3/2015 Christman ........... A61B 5/6897
345/174
(Continued)

FOREIGN PATENT DOCUMENTS

KR  10-2006-0081178 A   7/2006
KR   10-0650044 B1    11/2006
(Continued)

OTHER PUBLICATIONS

Haena Lee et al., Evaluation of PPG signals regarding to video attributes of smart-phone camera, Journal of the Korea Institute of Information and Communication Engineering, vol. 19, No. 4, Apr. 2015, pp. 917-924. (8 pages total).

(Continued)

*Primary Examiner* — Eric J Messersmith
(74) *Attorney, Agent, or Firm* — Sughrue Mion, PLLC

(57) ABSTRACT

An apparatus for measuring bio-information includes a pulse wave measurer configured to measure a pulse wave signal from a first region of an object; a contact pressure extractor including a touch screen and configured to obtain a contact pressure signal, indicating a contact pressure between the first region and the pulse wave measurer, based on touch data that is generated based on a second region of the object being in contact with the touch screen; and a processor configured to measure bio-information of the object based on the pulse wave signal and the contact pressure signal.

28 Claims, 22 Drawing Sheets

(51) Int. Cl.
  *A61B 5/00* (2006.01)
  *G06T 11/20* (2006.01)
  *A61B 5/02* (2006.01)
  *G06F 3/044* (2006.01)
  *A61B 5/103* (2006.01)
  *A61B 5/021* (2006.01)

(52) U.S. Cl.
  CPC ...... *A61B 5/02108* (2013.01); *A61B 5/02225* (2013.01); *A61B 5/02416* (2013.01); *A61B 5/02427* (2013.01); *A61B 5/1036* (2013.01); *A61B 5/681* (2013.01); *A61B 5/6826* (2013.01); *A61B 5/6843* (2013.01); *A61B 5/746* (2013.01); *G06F 3/044* (2013.01); *G06T 11/206* (2013.01)

(58) Field of Classification Search
  CPC ..... A61B 5/1036; A61B 5/6898; A61B 5/681; A61B 5/02427; A61B 5/6843; A61B 5/02416; A61B 5/02108; A61B 5/02007; A61B 5/02225; G06F 3/044; G06T 11/20; G06T 11/206
  See application file for complete search history.

(56) References Cited

U.S. PATENT DOCUMENTS

| | | |
|---|---|---|
| 2015/0374249 A1 | 12/2015 | Elliott et al. |
| 2016/0015301 A1 | 1/2016 | Elliott et al. |
| 2016/0256116 A1 | 9/2016 | Baik et al. |
| 2016/0374575 A1 | 12/2016 | Kim et al. |
| 2017/0251935 A1* | 9/2017 | Yuen ................ A61B 5/7278 |
| 2018/0310838 A1* | 11/2018 | Jeon ................ A61B 5/02116 |

FOREIGN PATENT DOCUMENTS

| | | |
|---|---|---|
| KR | 10-1022904 B1 | 3/2011 |
| KR | 10-2015-0119855 A | 10/2015 |
| KR | 10-2016-0108081 A | 9/2016 |

OTHER PUBLICATIONS

Search Report dated Mar. 14, 2019 by the European Patent Office in counterpart European Patent Application No. 18184922.5.

* cited by examiner

FIG. 3F

| 0 | 0 | 0 | 0 | 0 | 1 | 1 | 1 | 0 | 0 | 0 |
|---|---|---|---|---|---|---|---|---|---|---|
| 0 | 0 | 1 | 1 | 2 | 3 | 3 | 3 | 1 | 1 | 0 |
| 0 | 0 | 1 | 3 | 7 | 7 | 7 | 5 | 2 | 1 | 0 |
| 0 | 1 | 3 | 5 | 10 | 10 | 8 | 5 | 2 | 1 | 0 |
| 1 | 2 | 3 | 8 | 10 | 10 | 8 | 5 | 2 | 1 | 0 |
| 1 | 3 | 5 | 8 | 9 | 9 | 8 | 5 | 2 | 1 | 0 |
| 1 | 2 | 5 | 5 | 5 | 5 | 5 | 3 | 1 | 1 | 0 |
| 1 | 3 | 2 | 1 | 1 | 1 | 1 | 1 | 1 | 1 | 0 |
| 1 | 1 | 1 | 0 | 0 | 0 | 0 | 0 | 0 | 0 | 0 |

35

APPARATUS AND METHOD FOR MEASURING BIO-INFORMATION

CROSS-REFERENCE TO RELATED APPLICATION(S)

This application claims priority from Korean Patent Application No. 10-2017-0129256, filed on Oct. 11, 2017, in the Korean Intellectual Property Office, the entire disclosure of which is incorporated herein by reference for all purposes.

BACKGROUND

1. Field

Apparatuses and methods consistent with exemplary embodiments relate to an apparatus and a method for measuring bio-information, and more particularly, to a technology for non-invasively measuring bio-information such as blood pressure.

2. Description of Related Art

Generally, methods of non-invasively measuring blood pressure without damaging a human body include a method to measure blood pressure by measuring a cuff-based pressure and a method to estimate blood pressure by measuring a pulse wave without the use of a cuff.

A Korotkoff-sound method is one of cuff-based blood pressure measurement methods, in which a pressure in a cuff wound around an upper arm is increased and blood pressure is measured by listening to the sound generated in the blood vessel through a stethoscope while decreasing the pressure. Another cuff-based blood pressure measurement method is an oscillometric method using an automated machine, in which a cuff is wound around an upper arm, a pressure in the cuff is increased, a pressure in the cuff is continuously measured while the cuff pressure is gradually decreased, and blood pressure is measured based on a point where a change in a pressure signal is large.

Cuffless blood pressure measurement methods generally include a method of measuring blood pressure by calculating a pulse transit time (PTT) and a method a pulse wave analysis (PWA) method of estimating blood pressure by analyzing a shape of a pulse wave.

SUMMARY

One or more exemplary embodiments provide a bio-information measuring apparatus, a bio-information measuring method, and a wearable device including a bio-information measuring apparatus, in which bio-information such as blood pressure may be accurately measured without using a cuff According to an aspect of an exemplary embodiment, there is provided an apparatus for measuring bio-information, including: a pulse wave measurer configured to measure a pulse wave signal from a first region of an object; a contact pressure extractor including a touch screen and configured to obtain a contact pressure signal, indicating a contact pressure between the first region and the pulse wave measurer, based on touch data that is generated based on a second region of the object being in contact with the touch screen; and a processor configured to measure bio-information of the object based on the pulse wave signal and the contact pressure signal.

The contact pressure extractor may obtain the contact pressure signal based on at least one of a pixel intensity and a force value corresponding to the touch data, the touch data being generated based on the second region of the object that applies a pressure to the touch screen during measurement of the pulse wave signal from the first region.

The contact pressure extractor may determine a contact area based on the touch data and obtain the contact pressure signal based on at least one of a first result of summing pixel intensities corresponding to the contact area, a second result of summing force values corresponding to the contact area, and a third result of summing the pixel intensities and the force values corresponding to the contact area.

The contact pressure extractor may compensate the at least one of the first result, the second result, and the third result based on an area of the contact area and obtain the contact pressure signal based on a compensation result.

The apparatus may further include an outputter configured to, based on the second region being in contact with the touch screen, output information including at least one of information regarding a reference pressure to be applied by the second region to the touch screen during measurement of the pulse wave signal from the first region and information about a contact pressure applied by the second region to the touch screen.

The outputter may, based on receiving a request for measuring the bio-information, display an indication of an area to be in contact with the second region on the touch screen.

The outputter may output one or more of the measured pulse wave signal, the obtained contact pressure, and a processing result of the processor.

The apparatus may further include a storage configured to store information of a reference pressure to be applied by the second region to the touch screen during measurement of the pulse wave signal from the first region, the measured pulse wave signal, the obtained contact pressure, and a processing result of the processor.

The processor may determine a characteristic point based on the pulse wave signal and the contact pressure signal and measure the bio-information using the characteristic point and a measurement model.

The processor may generate a contact pressure versus pulse wave graph based on the pulse wave signal and the contact pressure signal and determine, as the characteristic point, at least one of a contact pressure value and a pulse wave value at a maximum peak point in the generated graph.

The processor may determine the characteristic point based on two or more pulse wave signals having different wavelengths, the two or more pulse wave signals being measured in a transition period of the contact pressure signal.

The characteristic point may include one or more from among a maximum point and/or a minimum point of each of the two or more pulse wave signals, a maximum point and/or a minimum point of a derivative signal obtained by differentiating each of the two or more pulse wave signals, a maximum point and/or a minimum point of a differential signal between the two or more pulse wave signals, a maximum point and/or a minimum point of a differential derivative signal of the differential signal, time and/or the contact pressure at each of maximum points and/or minimum points, a difference in time and/or the contact pressure between the maximum points and/or the minimum points, a ratio between a time difference and a contact pressure difference at each of the maximum points and/or the minimum points, a slope of each of the two or more pulse wave signals or the contact pressure signal, a value obtained by normalizing the slope of each of the two or more pulse wave signals with the slope of the contact pressure signal, a difference between slopes of the two or more pulse wave signals, a difference between values obtained by normalizing slopes of each of the two or more pulse wave signals, a time difference between the maximum point of each of the two or more pulse wave signals or the differential signal and the minimum point of each of the two or more pulse wave signals or a start point of the transition period, and a value obtained by normalizing the time difference with a slope of the contact pressure signal.

The bio-information may include one or more of a blood pressure, a vascular age, an arterial stiffness, an aortic artery pressure waveform, a vascular elasticity, a peripheral resistance, a stress index, and a fatigue level.

The apparatus may be provided in a wearable device, and wherein the touch screen is mounted on a first surface of a main body of the wearable device, and the pulse wave measurer includes at least one of an image sensor and a photoplethysmogram (PPG) sensor which is mounted on a second surface of the main body.

One of the first region and the second region may correspond to a thumb and another one of the first region and the second region may correspond to one of four fingers other than the thumb.

According to an aspect of another exemplary embodiment, there is provided a method of measuring bio-information, including: measuring, by a pulse wave measurer, a pulse wave signal from a first region of an object; obtaining a contact pressure signal indicating a contact pressure between the first region and the pulse wave measurer based on touch data that is generated based on a second region of the object being in contact with a touch screen; and measuring bio-information of the object based on the pulse wave signal and the contact pressure signal.

The obtaining the contact pressure signal may include obtaining the contact pressure signal based on at least one of a pixel intensity and a force value corresponding to the touch data, the touch data being generated based on the second region of the object that applies a pressure to the touch screen during measurement of the pulse wave signal from the first region.

The obtaining the contact pressure signal may further include determining a contact area based on the touch data and obtaining the contact pressure signal based on at least one of a first result of summing pixel intensities corresponding to the contact area, a second result of summing force values corresponding to the contact area, and a third result of summing the pixel intensities and the force values corresponding to the contact area.

The obtaining the contact pressure signal may include compensating the at least one of the first result, the second result, and the third result based on an area of the contact area and obtain the contact pressure signal based on a compensation result.

The method may further include, based on the second region being in contact with the touch screen, outputting one or more of information regarding a reference pressure to be applied by the second region to the touch screen during measurement of the pulse wave signal from the first region and information about a contact pressure applied by the second region to the touch screen.

The method may further include, based on receiving a request for measuring the bio-information, outputting an indication of an area to be in contact with the second region on the touch screen.

The method may further include outputting one or more of the measured pulse wave signal, the obtained contact pressure signal, and a result of measuring the bio-information.

The measuring the bio-information may include determining a characteristic point based on the pulse wave signal and the contact pressure signal and measuring the bio-information using the characteristic point and a measurement model.

The determining the characteristic point may include generating a contact pressure versus pulse wave graph based on the pulse wave signal and the contact pressure signal and determining, as the characteristic point, at least one of a contact pressure value and a pulse wave value at a maximum peak point in the generated graph.

The determining the characteristic point may include determining the characteristic point based on two or more pulse wave signals of different wavelengths, the two or more pulse wave signals being measured in a transition period of the contact pressure signal.

The characteristic point may include one or more from among a maximum point and/or a minimum point of each of the two or more pulse wave signals, a maximum point and/or a minimum point of a derivative signal obtained by differentiating each of the two or more pulse wave signals, a maximum point and/or a minimum point of a differential signal between the two or more pulse wave signals, a maximum point and/or a minimum point of a differential derivative signal of the differential signal, time and/or the contact pressure at each of maximum points and/or minimum points, a difference in time and/or the contact pressure between the maximum points and/or the minimum points, a ratio between a time difference and a contact pressure difference at each of the maximum points and/or the minimum points, a slope of each of the two or more pulse wave signals or the contact pressure signal, a value obtained by normalizing the slope of each of the two or more pulse wave signals with the slope of the contact pressure signal, a difference between slopes of the two or more pulse wave signals, a difference between values obtained by normalizing slopes of each of the two or more pulse wave signals, a time difference between the maximum point of each of the two or more pulse wave signals or the differential signal and the minimum point of each of the two or more pulse wave signals or a start point of the transition period, and a value obtained by normalizing the time difference with a slope of the contact pressure signal.

According to an aspect of still another exemplary embodiment, there is provided a wearable device including: a main body; a strap configured to be wrapped around an object; a pulse wave measurer mounted on a first surface of the main body and configured to measure a pulse wave signal from a first region of the object being in contact with the first surface of the main body; a contact pressure extractor mounted on a second surface of the main body and includes a touch screen, the contact pressure extractor configured to obtain a contact pressure signal, indicating a contact pressure between the first region and the pulse wave measurer, based on touch data which is generated based on a second region of the object being in contact with the touch screen; and a processor provided in the main body and configured to measure bio-information based on the pulse wave signal and the contact pressure signal.

The contact pressure extractor may obtain the contact pressure signal based on at least one of a pixel intensity and a force value corresponding to the touch data, the touch data being generated based on the second region of the object that applies a pressure to the touch screen during measurement of the pulse wave signal from the first region.

The contact pressure extractor may determine a contact area based on the touch data and obtain the contact pressure signal based on at least one of a first result of summing pixel intensities corresponding to the contact area, a second result of summing force values corresponding to the contact area, and a third result of summing the pixel intensities and the force values corresponding to the contact area.

The wearable device may further include an outputter configured to output at least one of information regarding a reference pressure to be applied by the second region to the touch screen, information about an actual contact pressure applied by the second region to the touch screen, and an area to be in contact with the second region.

The first region may correspond to a wrist of the object and the second region may correspond to a finger.

The wearable device may further include a communicator provided in the main body and configured to transmit at least one of the measured pulse wave signal, the obtained contact pressure signal, and a processing result of the processor to an external device.

The wearable device may further include a storage provided in the main body and configured to store at least one of the measured pulse wave signal, the obtained contact pressure signal, and a processing result of the processor.

The wearable device may further include an operator provided in the main body and configured to receive a command from a user and transmit the command to the processor.

BRIEF DESCRIPTION OF THE DRAWINGS

These and/or other aspects of the disclosure will become apparent and more readily appreciated from the following description of the exemplary embodiments, taken in conjunction with the accompanying drawings:

FIGS. 3A, 3B, 3C, 3D, 3E, 3F, and 3G are diagrams for describing a smart device to which the apparatus for measuring bio-information in accordance with the embodiments of FIGS. 1 and 2 is applied;

DETAILED DESCRIPTION

Figure 1:
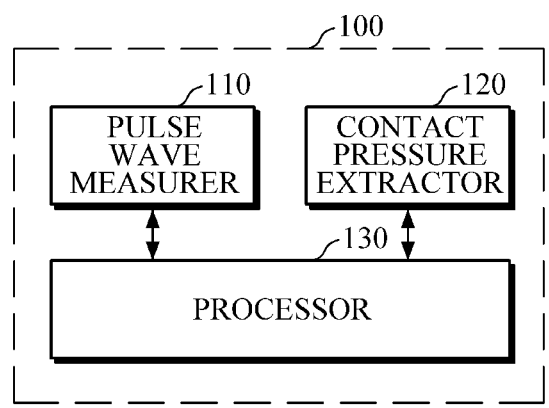
FIG. 1 is a block diagram illustrating an apparatus for measuring bio-information according to an exemplary embodiment.

Details of exemplary embodiments are provided in the following detailed description with reference to the accompanying drawings. The disclosure may be understood more readily by reference to the following detailed description of exemplary embodiments and the accompanying drawings. The disclosure may, however, be embodied in many different forms and should not be construed as being limited to the embodiments set forth herein. Rather, these embodiments are provided so that the disclosure will be thorough and complete and will fully convey the concept of the invention to those skilled in the art, and the disclosure will only be defined by the appended claims Like reference numerals refer to like elements throughout the specification.

It will be understood that, although the terms first, second, etc. may be used herein to describe various elements, these elements should not be limited by these terms. These terms are only used to distinguish one element from another. Also, the singular forms are intended to include the plural forms as well, unless the context clearly indicates otherwise. In the specification, unless explicitly described to the contrary, the word "comprise" and variations such as "comprises" or "comprising," will be understood to imply the inclusion of stated elements but not the exclusion of any other elements. Terms such as "unit" and "module" denote units that process at least one function or operation, and they may be implemented by using hardware, software, or a combination of hardware and software. Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

Hereinafter, embodiments of an apparatus and a method for measuring bio-information will be described in detail with reference to the accompanying drawings.

FIG. 1 is a block diagram illustrating an apparatus for measuring bio-information according to an exemplary embodiment.

Referring to FIG. 1, an apparatus 100 for measuring bio-information includes a pulse wave measurer 110, a contact pressure extractor 120, and a processor 130.

The pulse wave measurer 110 may measure a photoplethysmography (PPG) signal from an object. The pulse wave measurer 110 may include a pulse wave sensor. The pulse wave sensor may include a light emitter configured to emit light to a first region of the object and a light receiver configured to receive light scattered or reflected from a body tissue, such as a skin surface or a blood vessel, of the irradiated first region. The light emitter may include one or more light sources, for example, a light emitting diode (LED), a laser diode (LD), or a phosphor substance. The one or more light sources may emit light of different wavelengths from each other. The light receiver may include one or more detectors, for example, photodiodes, photo transistors (PTrs), or image sensors (e.g., complementary metal-oxide-semiconductor (CMOS) sensors). The one or more light sources may be disposed at different distances from the detector.

The contact pressure extractor 120 may obtain a contact pressure between the pulse wave measurer 110 and the object. For example, the contact pressure extractor 120 may include a touch screen. When a second region of the object is in contact with the touch screen, the contact pressure extractor 120 may receive touch data from the touch screen and extract a contact pressure using the received touch data. In this case, the touch screen may include a panel operating in a capacitive, resistive, infrared (IR), surface acoustic wave (SAW), electromagnetic (EM), or an electromagnetic resonance (EMR) manner.

For example, when the touch screen panel is a capacitive panel, the touch data generated by the touch screen may be a distribution of capacitance of each pixel. In this case, an intensity of a pixel may correspond to capacitance accumulated in each pixel when the second region of the object is in contact with the touch screen. Generally, when the second region of the object strongly presses the touch screen, the capacitance in the pixel may increase due to an increase of the contact time and the contact region.

The contact pressure extractor 120 may extract the contact pressure based on the pixel intensity of the touch data that changes according to a pressure applied to the touch screen as described above. For example, the contact pressure extractor 120 may extract a contact region of the touch screen with which the second region of the object is in contact from the touch data, and may extract the sum of the pixel intensities of the extracted contact region as the contact pressure. In addition, the contact pressure extractor 120 may calculate an area of the extracted contact region and extract the contact pressure P by compensating the sum F of the pixel intensities for the area A as shown in Equation 1 below. However, aspects of the disclosure are not limited thereto. For example, when the touch screen is a force touch screen, the contact pressure may be extracted based on a force value.

$$P = F/A \quad (1)$$

The pulse wave measurer 110 and the touch screen of the contact pressure extractor 120 may be mounted on opposite surfaces of a main body to which the apparatus 100 is applied. For example, the touch screen may be mounted to be exposure to a front surface of the main body and the pulse wave measurer 110 may be mounted to be exposed to a rear surface of the main body.

The user may generate touch data by touching the touch screen of the contact pressure extractor 120 located on the front surface of the main body with the second region of the object while touching the pulse wave measurer 110 located on the rear surface of the main body with the first region. In this case, the object may be a hand part of the user, for example, a finger. A first region may be one (e.g., index finger) of the four fingers other than the thumb and a second region may be the thumb, or vice versa, so that the user can obtain the pulse wave and a contact pressure while using his/her fingers like tweezers to grasp the main body. However, aspects of the disclosure are not limited thereto and the first region may be any other part of a body, such as an upper part of the wrist, a chest part, or an area under which the radial artery passes, and the second region may be fingers so that the second region applies pressure to the pulse wave measurer 110 while the pulse wave measurer 110 is in contact with the body part.

When contact is made with the pulse wave measurer 110 and the contact pressure extractor 120 (e.g., the touch screen) while the first region (e.g., index finger) and the second region (e.g., thumb) of the object hold the main body like a tweezers, a contact pressure between the first region and the pulse wave measurer 110 may have a value equal to or corresponding to a pressure exerted on the touch screen by the second region due to action and reaction. Therefore, the contact pressure extractor 120 may obtain the contact pressure between the first region and the pulse wave measurer 110 through touch data which is generated when the second region applies pressure to the touch screen.

The processor 130 may receive a bio-information measurement request from the user and control the pulse wave measurer 110 and the contact pressure extractor 120. The processor 130 may receive a pulse wave signal and a contact pressure signal from the pulse wave measurer 110 and the contact pressure extractor 120 and measure the bio-information based on the received pulse wave signal and contact pressure signal. In this case, the bio-information may include, but not limited to, systolic blood pressure, diastolic blood pressure, vascular age, arterial stiffness, aortic artery pressure waveform, vascular elasticity, stress index, fatigue level, and the like.

In PPG-based cuffless blood pressure measuring methods, there are problems in that PPG measurement is influenced by a contact pressure between the object and the pulse wave sensor because a change in the contact pressure between the object and the pulse wave sensor affects a shape of a PPG waveform. Therefore, the accuracy of estimating the blood pressure is degraded. In contrast, solutions according to an exemplary embodiment can solve these problems by obtaining the contact pressure between the first region of the object and the pulse wave measurer through touch data which is generated when the second region of the object applies pressure to the touch screen. Therefore, bio-information such as blood pressure can be accurately measured without being influenced by the contact pressure between the object and the pulse wave sensor. Also, according to an exemplary embodiment, accurate bio-information measurement can be performed even without using a pressure sensor.

Figure 2:
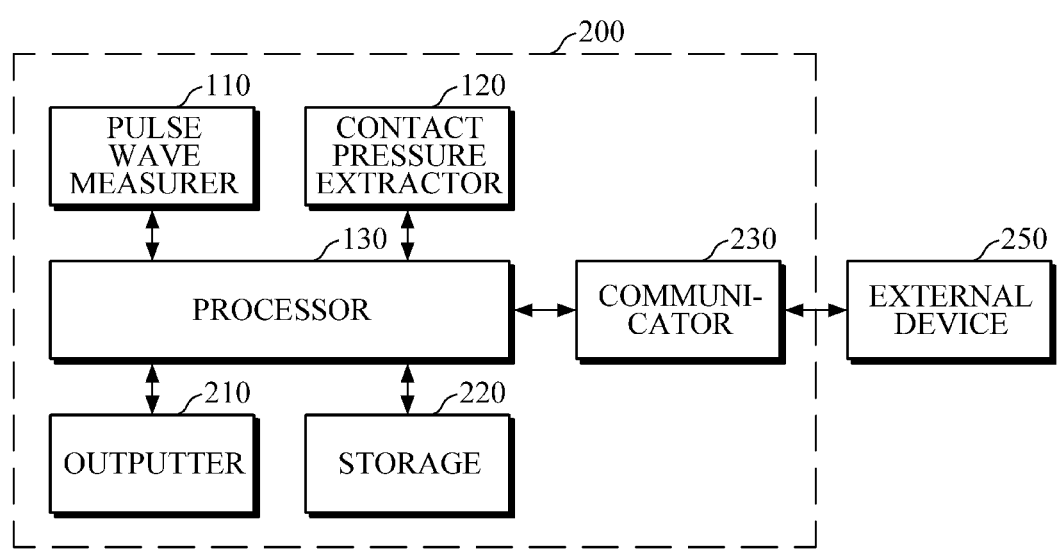
FIG. 2 is a block diagram illustrating an apparatus for measuring bio-information according to another exemplary embodiment.

FIG. 2 is a block diagram illustrating an apparatus for measuring bio-information according to another exemplary embodiment.

Referring to FIG. 2, the apparatus 200 for measuring bio-information includes a pulse wave measurer 110, a contact pressure extractor 120, a processor 130, an outputter 210, a storage 220, and a communicator 230. The pulse wave measurer 110, the contact pressure measurer 120, and the processor 130 are the same or similar to those described with reference to FIG. 1, and hence the following description will focus on other components.

The outputter 210 may output a processing result of the pulse wave measurer 110, the contact pressure extractor 120, or the processor 130. In this case, the outputter 210 may visually provide a variety of information to the user through a touch screen panel. Alternatively, the outputter 210 may provide the variety of information to the user through a speaker module or a haptic module in a non-visual manner, such as voice, vibration, or tactile sensation. For example, when measured blood pressure is out of a normal range, warning may be provided by displaying the blood pressure value in a red color or additional warning information may be provided via vibration or tactile sensation through a haptic module. The outputter 210 may include a speaker, a printer, a display, or any other output device.

In addition, the outputter 210 may output guidance information regarding the contact pressure. For example, when the outputter 210 receives a request for bio-information measurement from the user, an area with which the second region is to make contact may be displayed using a figure such as a rectangle or a circle on the touch screen panel or a center point at which the second region is to make contact may be displayed using a certain sign, for example, an arrow or a cross sign. In another example, when the second region is in contact with the touch screen, the outputter 210 may output an actual contact pressure of the second region extracted by the contact pressure extractor 120 to the touch screen panel. In another example, when a request for measuring bio-information is received, the outputter 210 may display an area to be in contact with the second region and also display reference pressure information in a predetermined area of the touch screen panel, or when the second region is in contact with the touch screen, the outputter 210 may display information regarding an actual contact pressure along with information regarding a reference pressure to be applied (or desired to be applied) by the second region.

The storage 220 may store a variety of reference information and a processing result of the pulse wave measurer 110, the contact pressure extractor 120, or the processor 130. In this case, the variety of reference information may include user information, such as age, sex, health condition, and the like, guidance information regarding the above-described contact pressure, or information necessary for bio-information estimation, such as a bio-information estimation model.

In this case, the storage 220 may include storage media, such as a flash memory, hard disk type memory, multimedia card micro type memory, a card-type memory (e.g., SD or XD memory, etc.), random access memory (RAM), static random access memory (SRAM), read-only memory (ROM), electrically erasable programmable read-only memory (EEPROM), programmable read-only memory (PROM), magnetic memory, a magnetic disk, an optical disk, and the like, but is not limited thereto.

The communicator 230 may communicate with the external device 250 under the control of the processor 130 and collaborate with the external device 250 to perform various operations related to the bio-information measurement. In one example, the communicator 230 may transmit the pulse wave measurement result, the contact pressure extraction result or the processing result of the processor 130 to the external device 250 to allow the external device 250 to monitor a user's health status and output bio-information history and a health status monitoring result. In this case, the external device 250 may include a smartphone, a tablet personal computer (PC), a desktop PC, a notebook PC, a device of a medical institute, but is not limited thereto. In another example, the communicator 230 may receive bio-information measurement model information, reference information for bio-information calibration, for example, information about cuff pressure, cuff blood pressure, and the like.

The communicator 230 may communicate with the external device using a Bluetooth communication, Bluetooth low energy (BLE) communication, near field communication (NFC), wireless local access network (WLAN) communication, ZigBee communication, ultra-wideband (UWB) communication, Ant+ communication, Wi-Fi communication, radio frequency identification (RFID) communication, $3^{rd}$ generation (3G) communication, 4G communication, 5G communication, or the like. However, these are merely examples, and aspects of the disclosure are not limited thereto.

FIGS. 3A to 3G are diagrams for describing a smart device to which the apparatus for measuring bio-information in accordance with the embodiments of FIGS. 1 and 2 is applied. In this case, the smart device may include a portable terminal, such as a smartphone or a tablet PC, and a device equipped with a touch screen panel and a pulse wave measurement sensor mounted on both sides of a main body, such as various types of wearable devices including a smart watch, a smart band, and the like.

Hereinafter, examples in which the smart device to which the apparatus 100 or 200 for measuring bio-information extracts a contact pressure will be described with reference to FIGS. 1 to 3G.

Figure 3A:
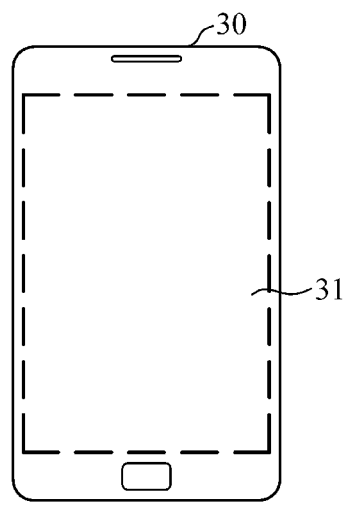
Figure 3B:
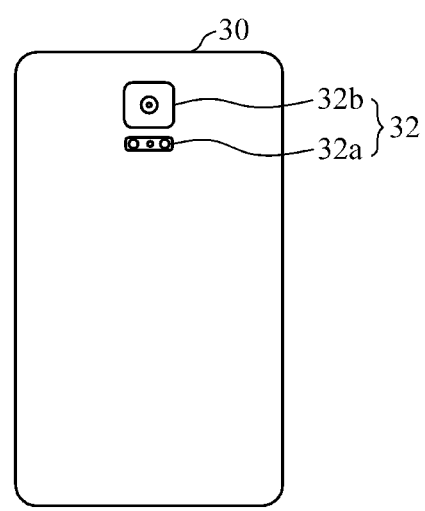

Referring to FIGS. 3A and 3B, a touch screen panel 31 of a contact pressure extractor 120 may be mounted on a front surface of a main body 30 of the smart device and a pulse wave sensor 32 of a pulse wave measurer 110 may be mounted on a rear surface of the main body 30 to be exposed to the outside. In this case, the pulse wave sensor 32 may include a light emitter 32a and a light receiver 32b. The light emitter 32a may be an LED and the light receiver 23b may be an image sensor. However, as described above, a dedicated PPG sensor may be mounted depending on the smart device.

Figure 3C:
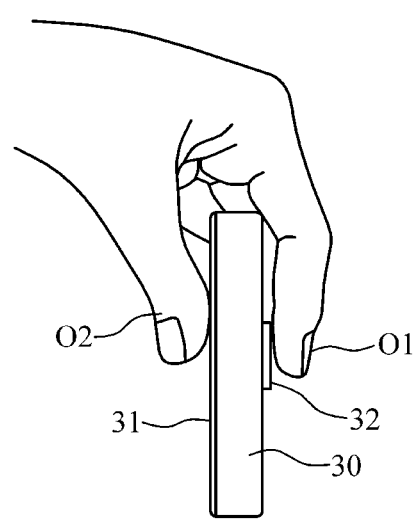

Referring to FIG. 3C, a first region of an object is an index finger 01 and a second region is a thumb 02. The user may change a pressure applied by the index finger 01 to the pulse wave sensor 32 by adjusting the strength of holding the main body 30 with the index finger 01 and the thumb 02 in a state in which the index finger 01 and the thumb 02 are in contact with the pulse wave sensor 32 and the touch screen 31, respectively, in order to measure bio-information. In this case, the forces exerted by the index finger 01 and the thumb 30 on the main body 30 may be the same or substantially correspond to each other due to action and reaction, and thus the contact pressure extractor 102 may acquire a contact pressure between the index finger 01 and the pulse wave sensor 32 by extracting a pressure exerted by the thumb 01 on the touch screen.

Figure 3D:
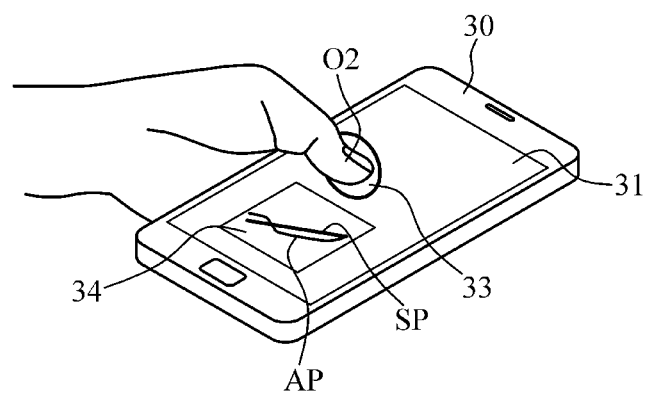

Referring to FIG. 3D, an outputter 210 may display information about an area 33 which the thumb 02, which is the second region of the object, is to be in contact with in a predetermined position of the touch screen panel 31. In addition, the outputter 210 may display reference pressure information SP in a predetermined area 34 of the touch screen panel 31, indicating a reference pressure which is to be applied by the thumb 02 to the touch screen while the pulse wave sensor 32 measures a pulse wave signal from the index finger 01. In addition, the outputter 201 may output actual contact pressure information AP extracted by the contact pressure extractor 120.

Figure 3E:
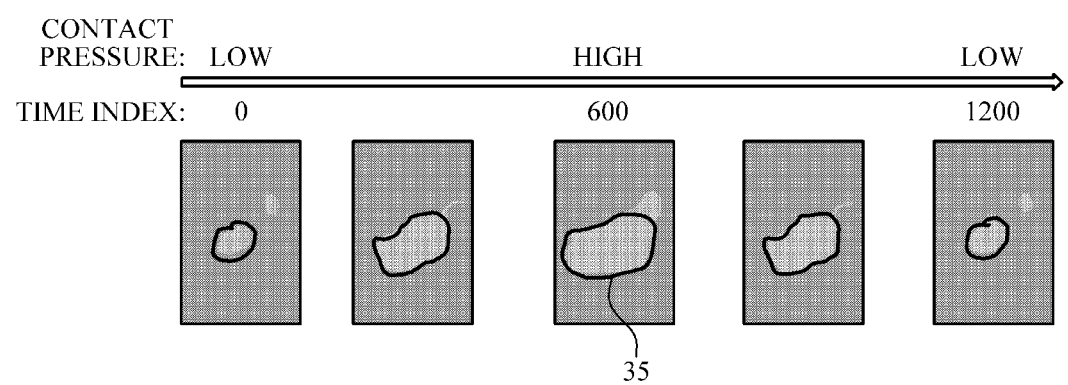

FIG. 3E shows imaged touch data of the touch screen when a pressure applied by the thumb is increased for a predetermined period of time and then decreased in a state where the thumb is in contact with the touch screen for a time between time index 0 and time index 1200. The third image in FIG. 3E represents touch data at a point in time where a time index is 600. As illustrated, a contact area of the touch screen is increased as the pressure on the touch screen increased, and the contact area of the touch screen is narrowed as the pressure is decreased.

The contact pressure extractor 120 may extract a region of interest (ROI) 35 based on the touch data being received from the touch screen. For example, the contact pressure extractor 120 images the touch data received from the touch screen as shown in FIG. 3E, and extract an ROI from the imaged touch data using a counter segmentation algorithm. Alternatively, the contact pressure extractor 120 may extract an area to be in contact with the thumb which is guided by the outputter 210 as the ROI.

Figure 3G:
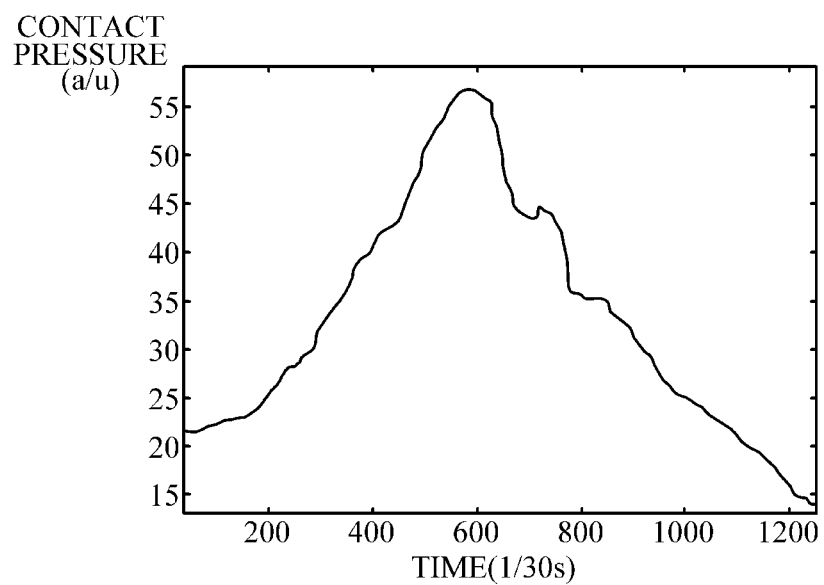

FIG. 3F is a diagram illustrating touch data at a point in time where a time index is 600, showing an intensity of each pixel generated when a pressure is applied to the touch screen by the thumb. FIG. 3G is a graph showing a contact pressure according to time elapsing from time index 0 to time index 1200.

Referring to FIG. 3F, the contact pressure extractor 120 may sum up the pixel intensities within the extracted ROI 35 and extract 215, which is the summing result, as a contact pressure. In this case, the contact pressure extractor 120 may normalize the pixel intensities and sum up the normalized values. In addition, the contact pressure extractor 120 may calculate an area of the ROI 35 and divide the sum of the pixel intensities by the calculated area to extract a division result or a normalized value of the division result as a contact pressure at a specific point in time. As such, when the force applied by the thumb to the touch screen is increased and then decreased during the time of measurement of a pulse wave from the index finger using the pulse wave measurer 110, the extracted contact pressure may be represented as shown in FIG. 3G.

Figure 4:
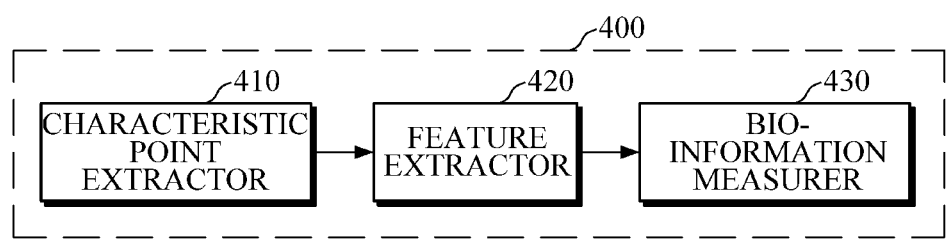
FIG. 4 is a diagram illustrating a configuration of the processors shown in FIGS. 1 and 2 according to an exemplary embodiment.
Figure 5A:
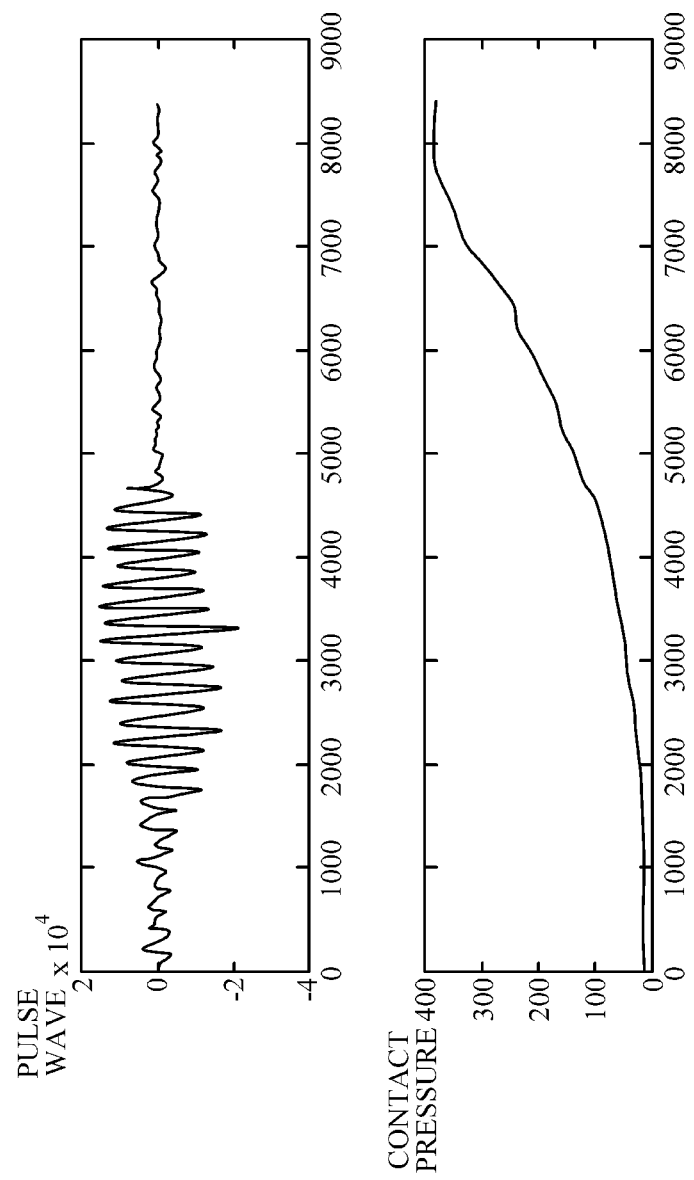
FIGS. 5A, 5B, and 5C are diagrams for describing feature extraction according to an exemplary embodiment.
Figure 5B:
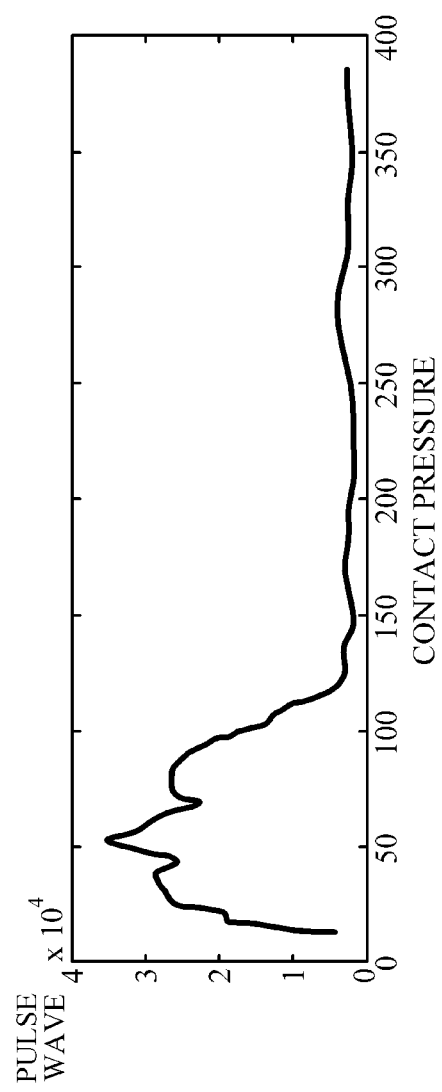
Figure 5C:
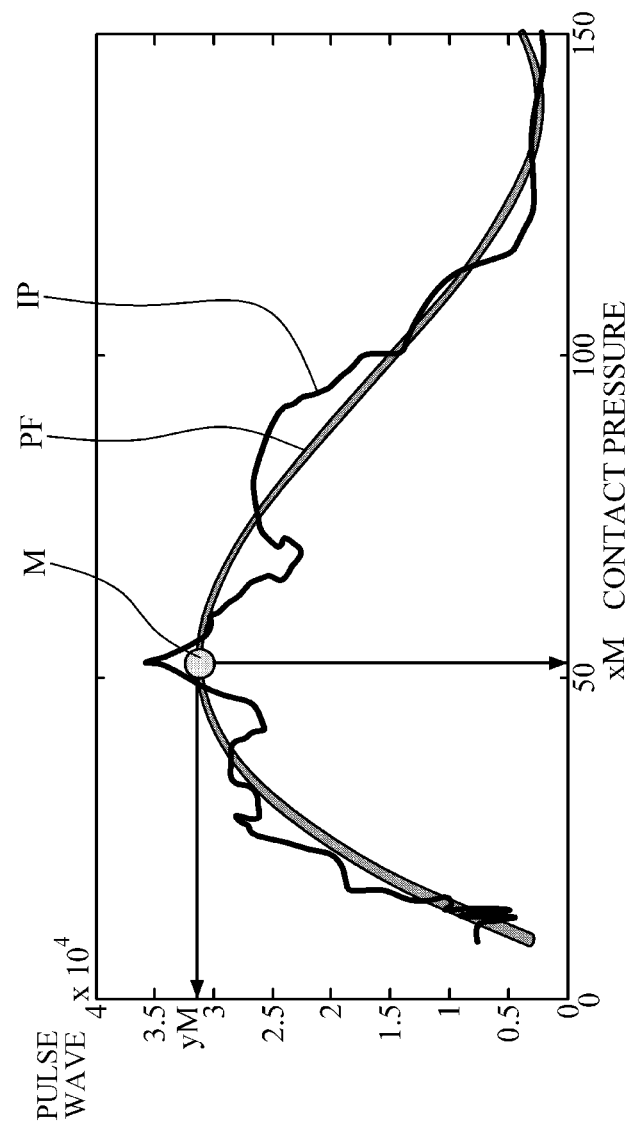

FIG. 4 is a diagram illustrating a configuration of the processors shown in FIGS. 1 and 2 according to an exemplary embodiment. FIGS. 5A to 5C are diagrams for describing feature extraction according to an exemplary embodiment. FIGS. 6A to 6F are diagrams for describing feature extraction according to another exemplary embodiment.

Referring to FIG. 4, the processor 400 according to an exemplary embodiment includes a characteristic point extractor 410, a feature extractor 420, and a bio-information measurer 430.

When the characteristic point extractor 410 receives a pulse wave signal and a contact pressure signal from a pulse wave measurer 110 and a contact pressure extractor 120, the characteristic point extractor 410 may extract a characteristic point to be used in measuring bio-information based on the pulse wave signal and the contact pressure signal.

The feature extractor 420 may extract a feature based on the extracted characteristic point. The feature extractor 420 may extract the feature by using one extracted characteristic point or combining two or more extracted characteristic points.

The bio-information measurer 430 may measure bio-information using the extracted feature. In this case, the bio-information may be measured by inputting the extracted feature to a bio-information measurement model.

An exemplary embodiment in which blood pressure is estimated based on an oscillometric method will be described with reference to FIGS. 4 to 5C.

FIG. 5A illustrates a pulse wave signal and a contact pressure signal which are obtained by gradually increasing a pressure applied by a second region of an object to a touch screen. FIG. 5B is a contact pressure versus pulse wave signal graph generated based on the contact pressure signal and the pulse wave signal.

Referring to FIGS. 5A and 5B, the characteristic point extractor 410 may extract a peak-to-peak point of the measured pulse wave signal waveform and generate the contact pressure versus pulse wave graph by plotting the peak-to-peak points at the same point in time based on the contact pressure value. In this case, the characteristic point extractor 410 may obtain an envelope of the pulse wave signal waveform that changes as the contact pressure applied to the touch screen is increased, and may extract a peak-to-peak point of the pulse wave signal waveform by subtracting a negative value from a positive value in the waveform at each measurement point in time using the obtained envelope of the pulse wave signal waveform.

FIG. 5C is a contact pressure versus pulse wave graph from which a characteristic point is extracted.

Referring to FIG. 5C, the characteristic point extractor 410 may extract a characteristic point using the contact pressure versus pulse wave graph. For example, the characteristic point extractor 410 may extract a contact pressure value or a pulse wave value at a point where a maximum peak occurs in the contact pressure versus pulse wave graph as the characteristic point. The characteristic point extractor 410 may perform a $3^{rd}$ polynomial fit of the contact pressure versus pulse wave graph IP and extract, as a characteristic point, a contact pressure value xM or a pulse wave value yM at the maximum peak point M in a graph PF obtained as a result of the $3^{rd}$ polynomial fit. However, aspects of the disclosure are not limited thereto.

When the contact pressure value xM or the pulse wave value yM is extracted at a point where the maximum peak occurs as described above, the feature extractor 420 may extract a feature used for measuring blood pressure by using the extracted characteristic point or combining two or more characteristic points. For example, the contact pressure value xM at the maximum peak point, which is extracted as the characteristic point, may be extracted as a feature for calculating a mean blood pressure (MBP). In addition, contact pressure values at the right and left points which are symmetrically distant from the contact pressure value xM at the maximum peak point and which have a pre-set peak ratio within a range from 0.5 to 0.7 may be extracted as features for calculating systolic blood pressure (SBP) and diastolic blood pressure (DBP).

When the features for measuring MBP, SBP, and DBP are extracted, the bio-information measurer 430 may input each of the extracted features to a bio-information measurement model to obtain MBP, SBP, and DBP. In this case, the bio-information measurement model may be constructed in advance in the form of a linear function as shown in Equation 2 below, but is not limited thereto. The bio-information measurement model may be constructed in advance in the form of a table in which characteristic points are mapped to blood pressure values.

$$y=ax+b \qquad (2)$$

Here, y denotes biometric information to be obtained, e.g., SBP, DBP, MBP, and the like, and x denotes the extracted feature. In addition, a and b are constant values obtained in advance through preprocessing, which may be defined differently according to the type of biometric information to be measured.

Various embodiments for extracting characteristic points and features related to blood recovery of a first region and estimating blood pressure based on the extracted features will be described with reference to FIG. 4 and FIGS. 6A to 6F.

When the strength of a second region of an object pressing on a touch screen is increased in a state in which the first region and the second region of the object of the user are in contact with a pulse wave sensor and the touch screen, respectively, the blood in the first region may be temporarily reduced due to the increase in the pressure on the pulse wave sensor and the color of the first region may turn white. When the strength of the second region pressing the touch screen is reduced, the blood re-circulates to the first region due to the decrease in the pressure on the pulse wave sensor and thus the color of the first region may turn red. Herein, such a characteristic is referred to as blood recovery. The blood recovery may be related to cardiovascular biomarker, such as blood velocity, pulse wave velocity, blood pressure, and the like.

The characteristic point extractor 410 may extract a characteristic point related to the blood recovery based on two or more pulse wave signals of different wavelengths and a pulse wave signal. The characteristic point extractor 410 may extract a transition period of the contact pressure signal and extract a characteristic point based on the pulse wave signal in the detected transition period. In this case, the transition period refers to a period in which a stable state (or non-pressurized state) is transited to a pressurized state, e.g., a period in which the contact pressure is increased, and a period in which the pressurized state is transited to the stable state, e.g., a period in which the contact pressure is decreased.

For example, the characteristic point related to the blood recovery may include one or more from among a maximum point and/or a minimum point of each of the pulse wave signals, a maximum point and/or a minimum point of a derivative signal obtained by differentiating each of the pulse wave signals, a maximum point and/or a minimum point of a differential signal between the pulse wave signals, a maximum point and/or a minimum point of a differential derivative signal of the differential signal, time and/or contact pressure at each of the maximum points and/or minimum points, a difference in time and/or contact pressure between the maximum points and/or minimum points, a ratio between time difference and contact pressure difference at each of the maximum points and/or a minimum points, a slope of each of the pulse wave signals or the contact pressure signal, a value obtained by normalizing the slope of each of the pulse wave signals with the slope of the contact pressure signal, a difference between slopes of the pulse wave signals, a difference between values obtained by normalizing slopes of each of the pulse wave signals, a time difference between a maximum point of each of the pulse wave signals or the differential signal and a minimum point or a start point of the transition period, and a value obtained by normalizing the time difference with a slope of the contact pressure signal.

The feature extractor 420 may extract the feature point for measuring blood pressure by using the extracted characteristic point or combining two or more of the extracted characteristic points.

Figure 6A:
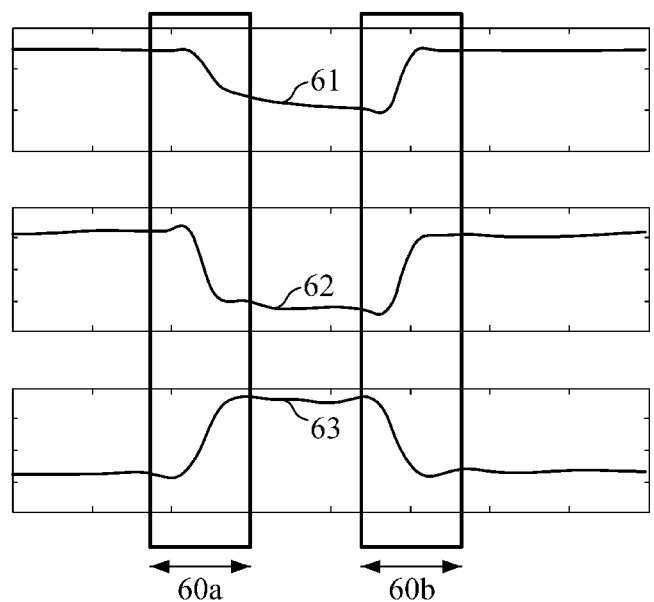
FIGS. 6A, 6B, 6C, 6D, 6E, and 6F are diagrams for describing feature extraction according to another exemplary embodiment.

Referring to FIG. 6A, the characteristic point extractor 410 may extract a first pulse wave DC component signal 61 and a second pulse wave DC component signal 62 by passing a first pulse wave signal (e.g., a pulse wave signal of a green wavelength) and a second pulse wave signal (e.g., a pulse wave signal of an infrared wavelength) through a low pass filter (LPF). In addition, the characteristic point extractor 410 may detect transition periods 60a and 60b of a contact pressure signal 63.

Figure 6B:
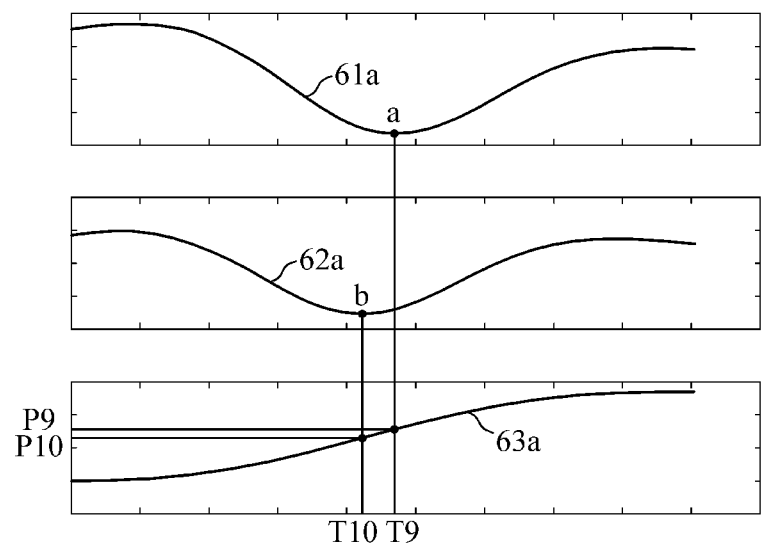

Referring to FIGS. 6A and 6B, the characteristic point extractor 410 may generate a first pulse wave DC component derivative signal 61a and a second pulse wave DC component derivative signal 62a by differentiating, respectively, the first pulse wave DC component signal 61 and the second pulse wave DC component signal 62 in the transition period in which a contact pressure is increased. The characteristic point extractor 410 may extract, as characteristic points related to the blood recovery, a time T9 and a contact pressure P9 corresponding to a minimum point a of the first pulse wave DC component derivative signal 61a and a time T10 and a contact pressure P10 corresponding to a minimum point b of the second pulse wave DC component derivative signal 62a.

Figure 6C:
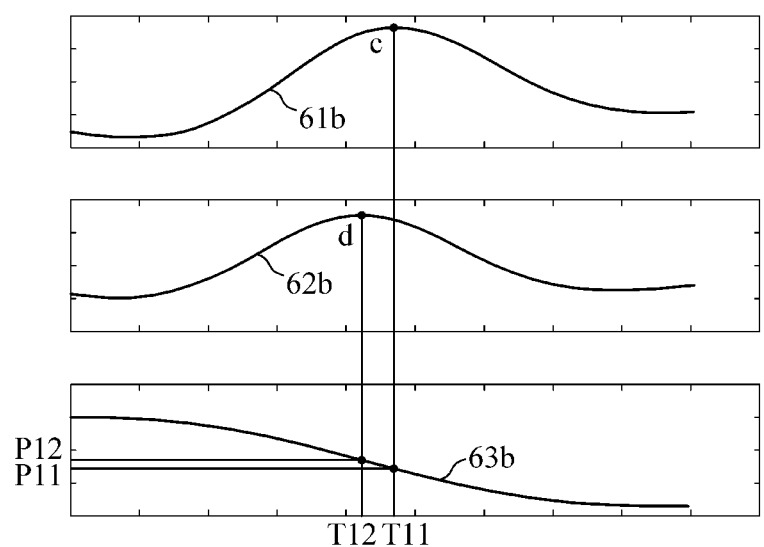

Referring to FIGS. 6A and 6C, the characteristic point extractor 410 may generate a first pulse wave DC component derivative signal 61b and a second pulse wave DC component derivative signal 62b by differentiating, respectively, the first pulse wave DC component signal 61 and the second pulse wave DC component signal 62 in a transition period 60b in which a contact pressure is decreased. The characteristic point extractor 410 may extract, as characteristic points related to the blood recovery, a time T11 and a contact pressure P11 corresponding to a maximum point c of the first pulse wave DC component derivative signal 61b and a time T12 and a contact pressure P12 corresponding to a maximum point d of the second pulse wave DC component derivative signal 62b.

Referring to FIGS. 6A to 6C, when the characteristic points are extracted as described above, the feature extractor 420 may extract a feature using Equation 3 below. In this case, Equation 3 is merely an example, and aspects of the disclosure are not limited thereto such that a feature may be extracted through various combinations of the characteristic points.

$$F = \left(\frac{P_{s1} - P_{s2}}{T_{s1} - T_{s2}}\right) \quad (3)$$

Here, F denotes a feature and $P_{s1}$ denotes the characteristic point P9 or P11 extracted using the first pulse wave DC component derivative signal 61a or 61b. $P_{s2}$ denotes the characteristic point P10 or P12 extracted using the second pulse wave DC component derivative signal 62a or 62b. $T_{s1}$ denotes the characteristic point T9 or T11 extracted using the first pulse wave DC component derivative signal 61a or 61b. $T_{s2}$ denotes the characteristic point T10 or T12 extracted using the second pulse wave DC component derivative signal 62a or 62b.

Figure 6D:
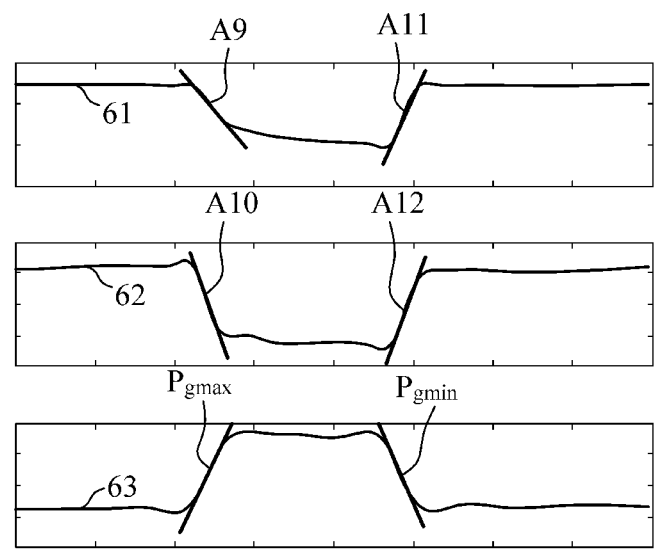

Referring to FIGS. 6A and 6D, the characteristic point extractor 410 may extract, as the characteristic points, a slope A9 of the first pulse wave DC component signal 61, a slope A10 of the second pulse wave DC component signal 62, and a slope $P_{gmax}$ of the contact pressure signal 63 in the transition period 60a in which the contact pressure is increased, and a slope A11 of the first pulse wave DC component signal 61, a slope A12 of the second pulse wave DC component signal 62 and a slope $P_{gmin}$ of the contact pressure signal 63 in the transition period 60b in which the contact pressure is decreased.

The feature extractor 420 may extract a feature related to the blood recovery through Equation 4 below. In this case, Equation 4 is merely an example and various combinations of the characteristic points may be used.

$$F = \frac{A_{s1} - A_{s2}}{P_g} \quad (4)$$

Here, F denotes a feature, $A_{s1}$ denotes the slope A9 or A11 of the first pulse wave DC component signal 61, and $A_{s2}$ denotes the slope A10 or A12 of the second pulse wave DC component signal 62. In addition, $P_g$ denotes the slope $P_{gmax}$ or $P_{gmin}$ of the contact pressure signal 63.

Figure 6E:
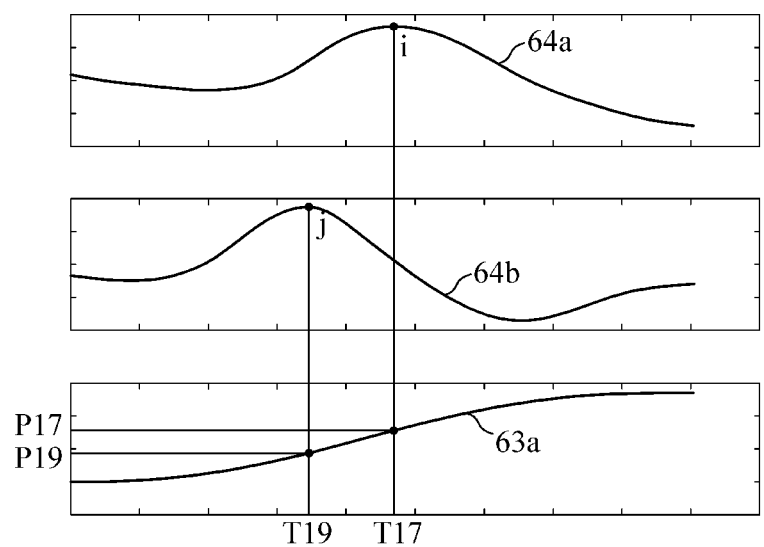

Referring to FIGS. 6A and 6E, the characteristic point extractor 410 may generate a DC component differential signal 64a by subtracting the second pulse wave DC component signal 62 from the first pulse wave DC component signal 61 in the transition period in which the contact pressure is increased. In addition, the characteristic point extractor 410 may generate a DC component differential derivate signal 64b by differentiating the DC component differential signal 64a. Moreover, the characteristic point extractor 410 may extract, as characteristic points, a time T17 and a contact pressure P17 corresponding to a maximum point i of the DC component differential signal 64a and a time T19 and a contact pressure P19 corresponding to a maximum point j of the DC component differential derivative signal 64b.

The feature extractor 420 may extract a feature by inputting the extracted characteristic points to the above-described Equation 3. In this case, $P_{s1}$ and $P_{s2}$ of Equation 3 denote the characteristic points P17 and P19, respectively. $T_{s1}$ and $T_{s2}$ denote the characteristic points T17 and T19, respectively.

Figure 6F:
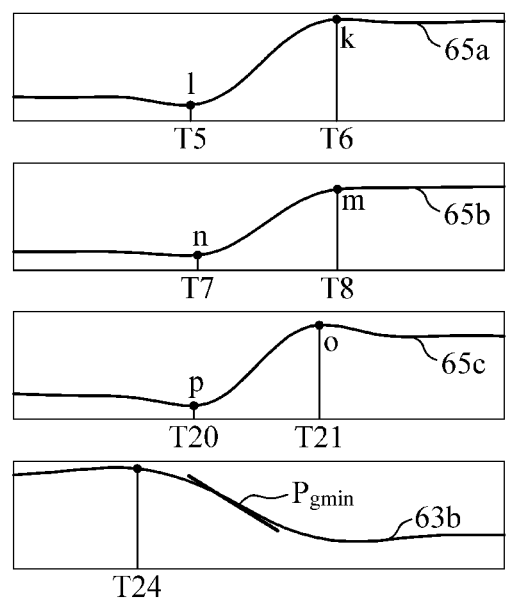

Referring to FIGS. 6A and 6F, the characteristic point extractor 410 may generate a DC component differential signal 65c by subtracting the second pulse wave DC component signal 65b from the first pulse wave DC component signal 65a in the transition period 60b in which the contact pressure is decreased. The characteristic point extractor 410 may extract, as characteristic points, times T5 and T6 corresponding to a minimum point I and a maximum point k of the first pulse wave DC component signal 65a, times T7 and T8 corresponding to a minimum point n and a maximum point m of the second pulse wave DC component signal 65b, times T20 and T21 corresponding to a minimum point p and a maximum point o of the DC component differential signal 65c, a slope $P_{gmin}$ of the contact pressure signal 63b in the transition period 60b in which the contact pressure is decreased, and a time T24 of a start point of the transition period 60b.

When the characteristic points are extracted as described above, the feature extractor 420 may extract a feature through Equation 5 below. Here, F denotes a feature, $T_{s1}$ denotes the characteristic point T6, T8, or T21, and $T_{s2}$ denotes the characteristic point T5, T7, T20, or T24.

$$F = \frac{T_{s1} - T_{s2}}{P_{gmin}} \quad (5)$$

Various embodiments for characteristic point extraction and feature extraction have been described with reference to FIGS. 6A to 6F. However, aspects of the disclosure are not limited thereto. For example, the characteristic point extractor 410 may generate a first pulse wave AC component signal and a second pulse wave AC component signal by passing the first pulse wave signal and the second pulse wave signal through a band pass filter (BPF) and characteristic points may be extracted using various methods based on the generated first pulse wave AC component signal, second pulse wave AC component signal, and the transition period of the contact pressure signal.

When the feature extractor 420 extracts the feature for measuring blood pressure, the bio-information measurer 430 may measure blood pressure using the extracted feature. For example, the bio-information measurer 430 may estimate blood pressure by inputting the extracted feature to a blood pressure measurement model such as Equation 2 as described above.

Figure 7:
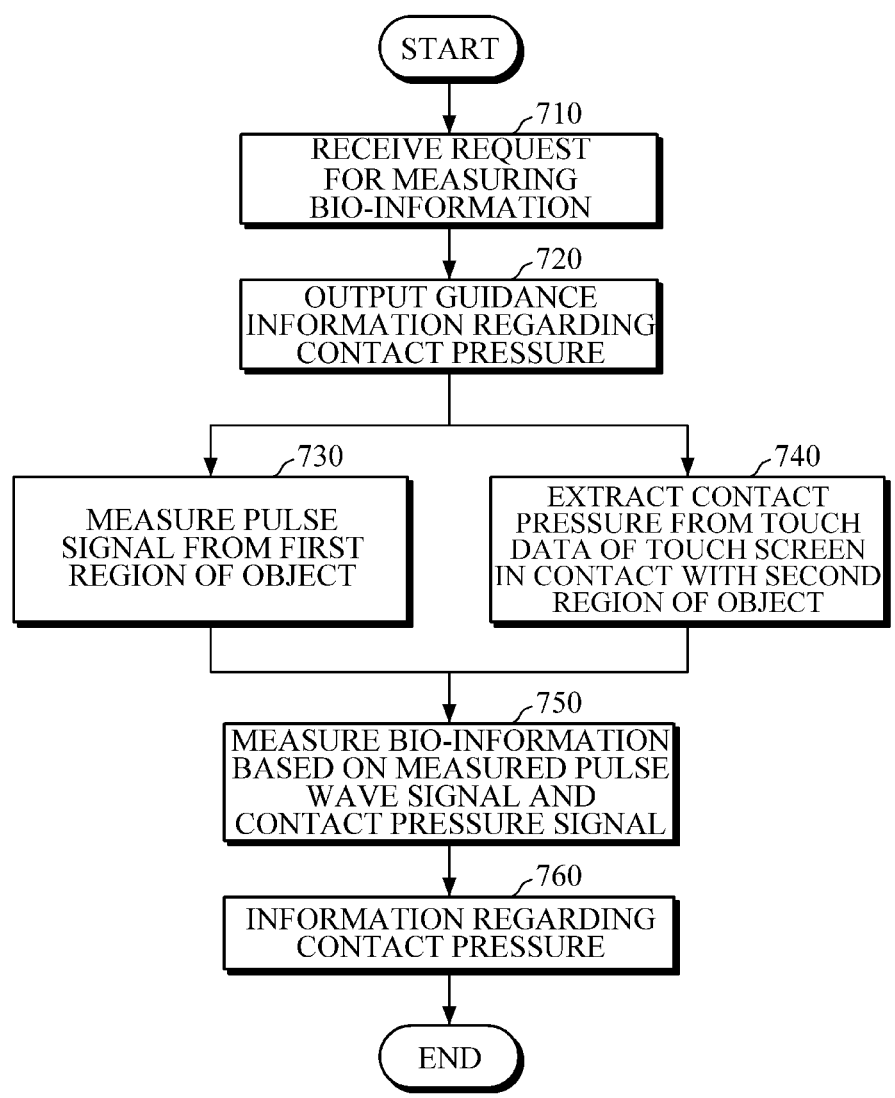
FIG. 7 is a flowchart illustrating a method of measuring bio-information according to an exemplary embodiment.

FIG. 7 is a flowchart illustrating a method of measuring bio-information according to an exemplary embodiment.

The method of FIG. 7 may be an exemplary embodiment of a bio-information measurement method performed by the apparatuses 100 and 200 of FIGS. 1 and 2.

First, when a request for measuring bio-information is received in operation 710, guidance information regarding a contact pressure is output to a user in operation 720. In this case, the guidance information regarding a contact pressure may be continuously provided to the user during the measurement of a pulse wave signal from a first region of an object. The guidance information regarding a contact pressure may include an area to be in contact with a second region of the object, information about a reference pressure to be applied by the second region to a touch screen, and information about an actual pressure applied by the second region to the touch screen in a state where the second region is in contact with the touch screen.

When the user changes a pressure applied by the second region to the touch screen according to the guidance information regarding the contact pressure in a state in which a first region and the second region are in contact with a pulse wave sensor and the touch screen, respectively, a pulse wave signal is measured from the first region in operation 730.

In addition, while the pulse wave signal is being measured from the first region, a contact pressure is extracted based on touch data generated from the touch screen in operation 740. For example, the area in contact with the first region may be extracted as an ROI from the touch data, and the contact pressure may be extracted based on a pixel intensity of the extracted ROI. For example, a value obtained by dividing the sum of pixel intensities of the ROI by an area of the ROI may be extracted as the contact pressure.

Bio-information is measured based on the pulse wave signal and contact pressure signal in operation 750. For example, as described above with reference to FIGS. 4 to 6F, characteristic points and a feature for measuring bio-information may be extracted based on an oscillometric method or the blood recovery and the bio-information may be measured using the extracted feature.

The information regarding contact pressure including the measured pulse wave signal, the contact pressure signal, the bio-information measurement result, warning, and/or alarm information may be output in operation 760.

Figure 8:
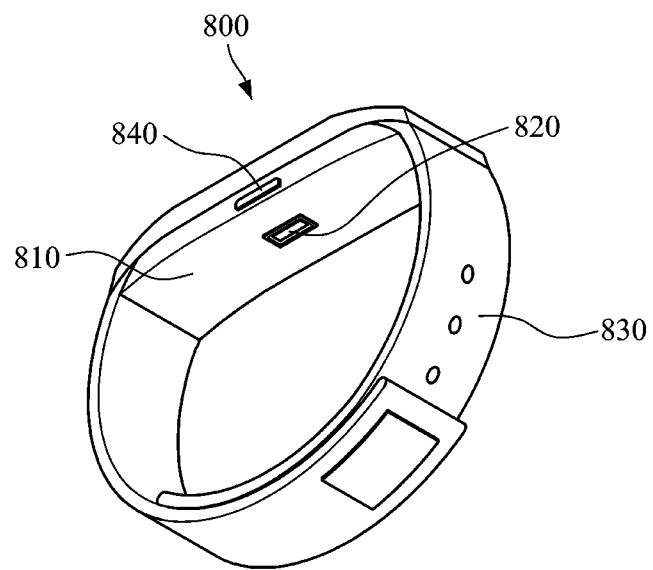
FIG. 8 is a diagram illustrating a wearable device according to an exemplary embodiment.
Figure 9:
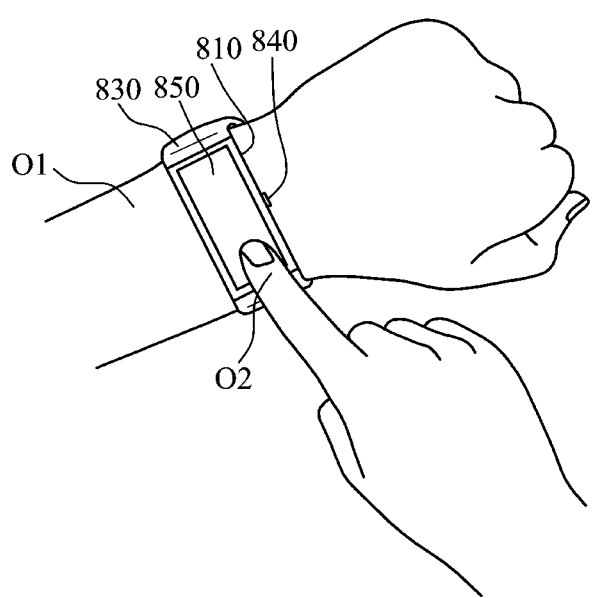
FIG. 9 is a diagram for describing signal measurement in the wearable device of FIG. 8.

FIG. 8 is a diagram illustrating a wearable device according to an exemplary embodiment. FIG. 9 is a diagram for describing signal measurement in the wearable device of FIG. 8. The wearable device 800 according to an exemplary embodiment is a wearable device that can be worn on a wrist, and the apparatus 100 or 200 for measuring bio-information according to the embodiment of FIG. 1 or 2 may be mounted thereon.

Referring to FIGS. 1, 2, 8 and 9, the wearable device 800 includes a main body 810 and a strap 830.

The strap 830 may be configured to be flexible and may be bent in such a manner that is wrapped around the wrist of the user or separated from the wrist. Alternatively, the strap 830 may be configured in the form of a non-separable band (e.g., continuous, integral form).

A battery may be equipped in the main body 810 or the strap 830 to supply power to the wearable device.

A pulse wave measurer 110 may be mounted on a rear surface of the main body 810 to measure a pulse wave signal from a first region O1 of an object. The pulse wave measurer 110 may include a pulse wave sensor 820 including a light emitter configured to emit light to the first region O1 and a detector configured to detect light scattered or reflected from the first region O1.

A contact pressure extractor 120 may be mounted on a front surface of the main body 810 to extract a contact pressure between the first region O1 and the pulse wave measurer 110. The contact pressure extractor 120 may include a touch screen panel 850 to generate touch data when a second region 02 of the object is in contact with the touch screen panel 850.

A processor 130 electrically connected to the pulse wave measurer 110 and the contact pressure extractor 120 may be mounted inside the main body 810. For example, when the user inputs a request for measuring bio-information in state in which the user is wearing the main body 810 on the object, e.g., a wrist, the processor 130 may generate a control signal to control the pulse wave measurer 110. In addition, the processor 130 may control an outputter 210 mounted in the main body 810 to output guidance information regarding a contact pressure.

When the user presses and releases the touch screen panel 850 with a finger O2 for a predetermined period of time according to the guidance information, the pulse wave measurer 110 may measure a pulse wave signal from an upper part O1 of the wrist and the contact pressure extractor 120 may extract a contact pressure based on touch data generated from the touch screen panel 850.

The processor 130 may receive the pulse wave signal and the contact pressure signal from the pulse wave measurer 110 and the contact pressure extractor 120, and measure bio-information based on the received pulse wave signal and contact pressure signal. For example, the processor 130 may extract characteristic points and feature related to an oscillometric method and/or blood recovery as described above, and measure blood pressure using the extracted feature.

In addition, the main body 810 may further include an operator 840 configured to receive a control command of the user and forward the control command to the processor 130. The operator 840 may include a power button for inputting a command for power on/off of the wearable device 800.

An outputter 210 may provide a user interface (UI) through the touch screen panel 850. The user may input various commands through touch input to the touch screen panel 850 or operation of the operator 840 via the provided user interface. The outputter 210 may output a variety of information related to bio-information, such as the guidance information regarding a contact pressure, the pulse wave signal and contact pressure signal, a bio-information measurement result, warning information, and the like. The outputter 210 may output the variety of information through various output modules mounted in the main body 810, such as the touch screen panel 850, a speaker module (e.g., a speaker), and a haptic module (e.g., a vibrator or vibration motor).

In addition, the main body 810 may further include a storage 220 in which the variety of information related to the bio-information, such as user information, the guidance information regarding a contact pressure, the pulse wave signal and contact pressure signal, the bio-information measurement result, and/or warning information is stored.

Additionally, the main body 810 may further include a communicator 230 for communications with an external device, such as a portable terminal of the user. The communicator 230 may receive a bio-information measurement model that is used for bio-information measurement, reference information (e.g., cuff pressure, cuff blood pressure, etc.) for calibration of the bio-information measurement model, and the like from the external device. Furthermore, the communicator 230 may request the measurement of bio-information by transmitting the extracted characteristic points or feature information to the external device. In addition, the communicator 230 may transmit the bio-information measurement result to the external device to display the measurement result to the user or allow the measurement result to be utilized for various purposes, such as bio-information history management, disease research, and the like.

The exemplary embodiments can be implemented as computer readable codes in a computer readable record medium. Codes and code segments of the computer program according to the exemplary embodiments can be easily inferred by a skilled computer programmer in the art. The computer readable record medium includes all types of record media in which computer readable data are stored. Examples of the computer readable record medium include a ROM, a RAM, a CD-ROM, a magnetic tape, a floppy disk, and an optical data storage. Further, the record medium may be implemented in the form of a carrier wave such as Internet transmission. In addition, the computer readable record medium may be distributed to computer systems over a network, in which computer readable codes may be stored and executed in a distributed manner.

At least one of the components, elements, modules or units represented by a block as illustrated in the drawings may be embodied as various numbers of hardware, software and/or firmware structures that execute respective functions described above, according to an exemplary embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in the above block diagrams, communication between the components, elements or units may be performed through the bus. Functional aspects of the above exemplary embodiments may be implemented in algorithms that execute on one or more processors. Furthermore, the components, elements or units represented by a block or processing steps may employ any number of related art techniques for electronics configuration, signal processing and/or control, data processing and the like.

Although a few embodiments have been shown and described, it would be appreciated by those skilled in the art that changes may be made in the example embodiments without departing from the principles and spirit of the disclosure, the scope of which is defined in the claims and their equivalents.

What is claimed is:

1. An apparatus for measuring bio-information, comprising:
   a pulse wave measurer configured to measure a pulse wave signal from a first region of an object;
   a contact pressure extractor comprising a touch screen and configured to obtain a contact pressure signal, indicating a contact pressure between the first region and the pulse wave measurer, based on touch data that is generated based on a second region of the object being in contact with the touch screen; and
   a processor configured to determine a characteristic point based on two or more pulse wave signals having different wavelengths, the two or more pulse wave signals being measured in a transition period of the contact pressure signal, and measure the bio-information of the object using the characteristic point and a measurement model.

2. The apparatus of claim 1, wherein the contact pressure extractor is further configured to obtain the contact pressure signal based on at least one of a pixel intensity and a force value corresponding to the touch data, the touch data being generated based on the second region of the object that applies a pressure to the touch screen during measurement of the pulse wave signal from the first region.

3. The apparatus of claim 2, wherein the contact pressure extractor is further configured to determine a contact area based on the touch data and obtain the contact pressure signal based on at least one of a first result of summing pixel intensities corresponding to the contact area, a second result of summing force values corresponding to the contact area, and a third result of summing the pixel intensities and the force values corresponding to the contact area.

4. The apparatus of claim 3, wherein the contact pressure extractor is further configured to compensate the at least one of the first result, the second result, and the third result based on an area of the contact area and obtain the contact pressure signal based on a compensation result.

5. The apparatus of claim 1, further comprising an outputter configured to, based on the second region being in contact with the touch screen, output information including at least one of information regarding a reference pressure to be applied by the second region to the touch screen during measurement of the pulse wave signal from the first region and information about a contact pressure applied by the second region to the touch screen.

6. The apparatus of claim 5, wherein the outputter is further configured to, based on receiving a request for measuring the bio-information, display an indication of an area to be in contact with the second region on the touch screen.

7. The apparatus of claim 5, wherein the outputter is further configured to output one or more of the measured pulse wave signal, the obtained contact pressure, and a processing result of the processor.

8. The apparatus of claim 1, further comprising a storage configured to store information of a reference pressure to be applied by the second region to the touch screen during measurement of the pulse wave signal from the first region, the measured pulse wave signal, the obtained contact pressure, and a processing result of the processor.

9. The apparatus of claim 1, wherein the characteristic point comprises one or more from among a maximum point and/or a minimum point of each of the two or more pulse wave signals, a maximum point and/or a minimum point of a derivative signal obtained by differentiating each of the two or more pulse wave signals, a maximum point and/or a minimum point of a differential signal between the two or more pulse wave signals, a maximum point and/or a minimum point of a differential derivative signal of the differential signal, time and/or the contact pressure at each of maximum points and/or minimum points, a difference in time and/or the contact pressure between the maximum points and/or the minimum points, a ratio between a time difference and a contact pressure difference at each of the maximum points and/or the minimum points, a slope of each of the two or more pulse wave signals or the contact pressure signal, a value obtained by normalizing the slope of each of the two or more pulse wave signals with the slope of the contact pressure signal, a difference between slopes of the two or more pulse wave signals, a difference between values obtained by normalizing slopes of each of the two or more pulse wave signals, a time difference between the maximum point of each of the two or more pulse wave signals or the differential signal and the minimum point of each of the two or more pulse wave signals or a start point of the transition period, and a value obtained by normalizing the time difference with a slope of the contact pressure signal.

10. The apparatus of claim 1, wherein the bio-information comprises one or more of a blood pressure, a vascular age, an arterial stiffness, an aortic artery pressure waveform, a vascular elasticity, a peripheral resistance, a stress index, and a fatigue level.

11. The apparatus of claim 1, wherein the apparatus is provided in a wearable device, and
wherein the touch screen is mounted on a first surface of a main body of the wearable device, and the pulse wave measurer comprises at least one of an image sensor and a photoplethysmogram (PPG) sensor which is mounted on a second surface of the main body.

12. The apparatus of claim 11, wherein one of the first region and the second region corresponds to a thumb and another one of the first region and the second region corresponds to one of four fingers other than the thumb.

13. A method of measuring bio-information, comprising:
measuring, by a pulse wave measurer, a pulse wave signal from a first region of an object;
obtaining a contact pressure signal indicating a contact pressure between the first region and the pulse wave measurer based on touch data that is generated based on a second region of the object being in contact with a touch screen; and
determining a characteristic point based on two or more pulse wave signals of different wavelengths, the two or more pulse wave signals being measured in a transition period of the contact pressure signal, and measuring bio-information of the object using the characteristic point and a measurement model.

14. The method of claim 13, wherein the obtaining the contact pressure signal comprises obtaining the contact pressure signal based on at least one of a pixel intensity and a force value corresponding to the touch data, the touch data being generated based on the second region of the object that applies a pressure to the touch screen during measurement of the pulse wave signal from the first region.

15. The method of claim 14, wherein the obtaining the contact pressure signal further comprises determining a contact area based on the touch data and obtaining the contact pressure signal based on at least one of a first result of summing pixel intensities corresponding to the contact area, a second result of summing force values corresponding to the contact area, and a third result of summing the pixel intensities and the force values corresponding to the contact area.

16. The method of claim 15, wherein the obtaining the contact pressure signal comprises compensating the at least one of the first result, the second result, and the third result based on an area of the contact area and obtain the contact pressure signal based on a compensation result.

17. The method of claim 13, further comprising, based on the second region being in contact with the touch screen, outputting one or more of information regarding a reference pressure to be applied by the second region to the touch screen during measurement of the pulse wave signal from the first region and information about a contact pressure applied by the second region to the touch screen.

18. The method of claim 17, further comprising, based on receiving a request for measuring the bio-information, outputting an indication of an area to be in contact with the second region on the touch screen.

19. The method of claim 13, further comprising outputting one or more of the measured pulse wave signal, the obtained contact pressure signal, and a result of measuring the bio-information.

20. The method of claim 13, wherein the characteristic point comprises one or more from among a maximum point and/or a minimum point of each of the two or more pulse wave signals, a maximum point and/or a minimum point of a derivative signal obtained by differentiating each of the two or more pulse wave signals, a maximum point and/or a minimum point of a differential signal between the two or more pulse wave signals, a maximum point and/or a minimum point of a differential derivative signal of the differential signal, time and/or the contact pressure at each of maximum points and/or minimum points, a difference in time and/or the contact pressure between the maximum points and/or the minimum points, a ratio between a time difference and a contact pressure difference at each of the maximum points and/or the minimum points, a slope of each of the two or more pulse wave signals or the contact pressure signal, a value obtained by normalizing the slope of each of the two or more pulse wave signals with the slope of the contact pressure signal, a difference between slopes of the two or more pulse wave signals, a difference between values obtained by normalizing slopes of each of the two or more pulse wave signals, a time difference between the maximum point of each of the two or more pulse wave signals or the differential signal and the minimum point of each of the two or more pulse wave signals or a start point of the transition period, and a value obtained by normalizing the time difference with a slope of the contact pressure signal.

21. A wearable device comprising:
a main body;
a strap configured to be wrapped around an object;
a pulse wave measurer mounted on a first surface of the main body and configured to measure a pulse wave signal from a first region of the object being in contact with the first surface of the main body;
a contact pressure extractor mounted on a second surface of the main body and comprises a touch screen, the contact pressure extractor configured to obtain a contact pressure signal, indicating a contact pressure between the first region and the pulse wave measurer, based on touch data which is generated based on a second region of the object being in contact with the touch screen; and
a processor provided in the main body and configured to determine a characteristic point based on two or more pulse wave signals having different wavelengths, the two or more pulse wave signals being measured in a transition period of the contact pressure signal, and measure the bio-information of the object using the characteristic point and a measurement model.

22. The wearable device of claim 21, wherein the contact pressure extractor is further configured to obtain the contact pressure signal based on at least one of a pixel intensity and a force value corresponding to the touch data, the touch data being generated based on the second region of the object that applies a pressure to the touch screen during measurement of the pulse wave signal from the first region.

23. The wearable device of claim 22, wherein the contact pressure extractor is further configured to determine a contact area based on the touch data and obtain the contact pressure signal based on at least one of a first result of summing pixel intensities corresponding to the contact area, a second result of summing force values corresponding to the contact area, and a third result of summing the pixel intensities and the force values corresponding to the contact area.

24. The wearable device of claim 21, further comprising an outputter configured to output at least one of information regarding a reference pressure to be applied by the second region to the touch screen, information about an actual contact pressure applied by the second region to the touch screen, and an area to be in contact with the second region.

25. The wearable device of claim 21, wherein the first region corresponds to a wrist of the object and the second region corresponds to a finger.

26. The wearable device of claim 21, further comprising a communicator provided in the main body and configured to transmit at least one of the measured pulse wave signal, the obtained contact pressure signal, and a processing result of the processor to an external device.

27. The wearable device of claim 21, further comprising a storage provided in the main body and configured to store at least one of the measured pulse wave signal, the obtained contact pressure signal, and a processing result of the processor.

28. The wearable device of claim 21, further comprising an operator provided in the main body and configured to receive a command from a user and transmit the command to the processor.

* * * * *